(12) United States Patent
Chan

(10) Patent No.: US 9,332,931 B2
(45) Date of Patent: May 10, 2016

(54) PULSATING EXPRESSION CAP

(75) Inventor: Frank A. Chan, Sunnyvale, CA (US)

(73) Assignee: Roche Diabetes Care, Inc., Indianapolis, IN (US)

(*) Notice: Subject to any disclaimer, the term of this patent is extended or adjusted under 35 U.S.C. 154(b) by 1079 days.

(21) Appl. No.: 12/244,802

(22) Filed: Oct. 3, 2008

(65) Prior Publication Data

US 2009/0124930 A1    May 14, 2009

Related U.S. Application Data

(63) Continuation of application No. 11/680,099, filed on Feb. 28, 2007, now abandoned, which is a continuation of application No. 10/809,725, filed on Mar. 25, 2004, now Pat. No. 7,201,723.

(51) Int. Cl.
   *A61B 5/15*   (2006.01)

(52) U.S. Cl.
   CPC .................... *A61B 5/1411* (2013.01)

(58) Field of Classification Search
   CPC ...................................................... A61B 5/1411
   USPC ................... 600/573, 576, 583; 606/181, 182
   See application file for complete search history.

(56) References Cited

U.S. PATENT DOCUMENTS

| | | | |
|---|---|---|---|
| 1,579,679 A | 4/1926 | Wahrt | |
| 2,067,991 A | 1/1937 | Taylor | |
| 2,646,799 A | 7/1953 | Jacoby, Jr. | |
| 3,623,475 A | 11/1971 | Sanz | |
| 3,626,929 A | 12/1971 | Sanz et al. | |
| 4,509,517 A | 4/1985 | Zibelin | |
| 5,014,718 A | 5/1991 | Mitchen | |
| 5,159,922 A | 11/1992 | Mabuchi et al. | |
| 5,318,584 A | 6/1994 | Lange et al. | |
| 5,447,491 A | 9/1995 | Bellandi | |
| 5,540,709 A | 7/1996 | Ramel | |
| 5,662,362 A | 9/1997 | Kapgan et al. | |
| 5,843,006 A | 12/1998 | Phillips et al. | |
| 5,951,493 A | 9/1999 | Douglas et al. | |
| 5,964,718 A | 10/1999 | Duchon et al. | |
| 6,056,765 A | 5/2000 | Bajaj et al. | |
| 6,086,545 A | 7/2000 | Roe et al. | |
| 6,319,210 B1 | 11/2001 | Douglas et al. | |
| 6,332,871 B1 | 12/2001 | Douglas et al. | |
| 6,537,242 B1 | 3/2003 | Palmer | |
| 6,547,764 B2 | 4/2003 | Larsen et al. | |
| 6,752,817 B2 | 6/2004 | Flora et al. | |
| 7,201,723 B2 | 4/2007 | Chan | |
| 7,658,709 B2 * | 2/2010 | Anderson et al. | 600/143 |
| 2002/0087180 A1 | 7/2002 | Searle et al. | |
| 2002/0103499 A1 | 8/2002 | Perez et al. | |
| 2002/0188223 A1 | 12/2002 | Perez et al. | |
| 2005/0085839 A1 | 4/2005 | Allen et al. | |

FOREIGN PATENT DOCUMENTS

| | | |
|---|---|---|
| JP | 2002-065648 | 3/2002 |
| WO | WO 02/100276 | 12/2002 |

* cited by examiner

*Primary Examiner* — Rene Towa
(74) *Attorney, Agent, or Firm* — Woodard, Emhardt, Moriarty, McNett & Henry LLP

(57) ABSTRACT

A body fluid sampling device includes an expression member placed around an incision in the skin of a user, a compression member to contact and traverse the expression member, and a housing configured to contact the skin near the incision. The expression member is configured to repeatedly move from a relaxed position over the incision to a contracted position over the incision. The expression member is at least partially resilient in order to repeatedly squeeze and/or compress the skin around the incision.

13 Claims, 10 Drawing Sheets

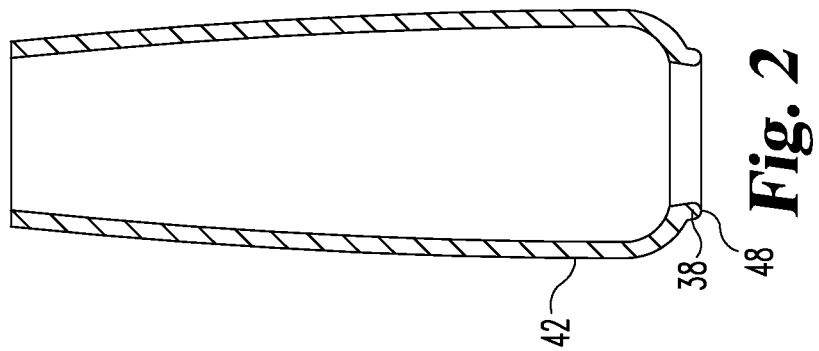
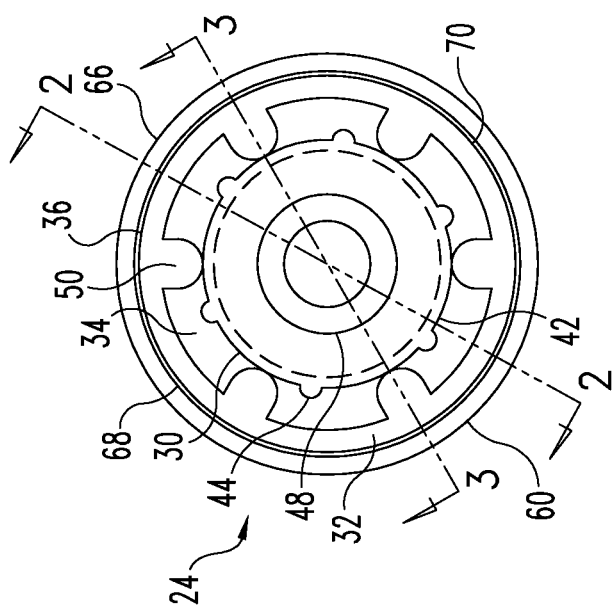

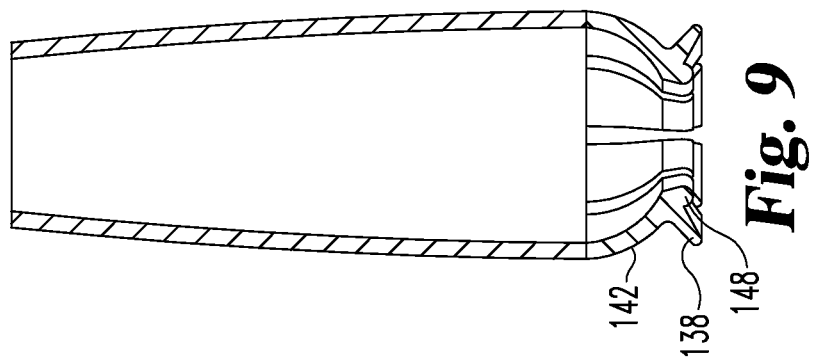
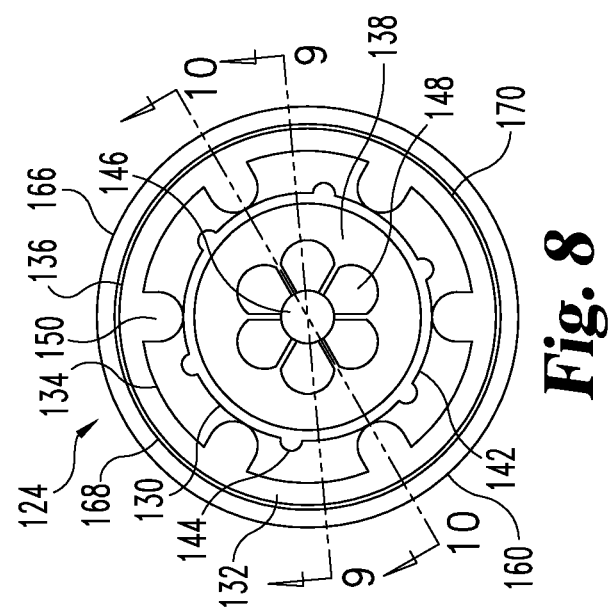

PULSATING EXPRESSION CAP

CROSS REFERENCE TO RELATED APPLICATIONS

This application is a continuation of U.S. patent application Ser. No. 11/680,099, filed Feb. 28, 2007, now abandoned, which is a continuation of U.S. patent application Ser. No. 10/809,725 filed Mar. 25, 2004, now U.S. Pat. No. 7,201,723, both of which are hereby incorporated by reference.

BACKGROUND OF THE INVENTION

The present invention generally relates to body fluid sampling devices, and more specifically, but not exclusively, concerns a sampling device and a technique for expressing body fluid with the device.

The testing of bodily fluids basically involves the steps of making an incision in the patient's skin, expressing the fluid sample, collecting the fluid sample, transferring the sample to a test device, conducting a test on the fluid sample, and displaying the results. These steps are generally performed by a plurality of separate instruments or devices. Typically, an incision is formed in the fingertip of a patient in order to obtain a body fluid sample. Patients are frequently advised to urge fluid to the incision site.

Patients may urge fluid to the incision site on a finger by applying and releasing pressure to a region of skin near the incision with a finger massaging device. In this application, patients frequently use the finger massaging device that applies and releases pressure to a specific region of skin near the incision. The user inserts his finger into the device and pressure is repeatedly applied and released to specific points on the finger.

Often patients try to manually pump or milk the fluid from the incision by applying pressure to the skin. Manually applying pressure to the area surrounding the incision may be difficult for patients, especially for patients with limited hand dexterity, such as the elderly. Therefore, patients may try to use a mechanical device to express bodily fluid from an incision.

One problem associated with the finger massaging device is that portions of skin surrounding the incision are not massaged. Therefore a patient will not be able to urge as much bodily fluid to the incision when compared to the situation wherein all of the skin surrounding the incision is massaged. If an adequate amount of bodily fluid is not expressed to the incision site, then the patient may have to incise another area of skin.

The finger massaging device does not apply oscillating pressure against the skin surrounding the incision. Rather, the device applies oscillating pressure to the skin of the finger on the side opposite the incision. Moreover, the finger massaging device does not vary the pattern of pressure. Therefore, an adequate amount of fluid may not be expressed. Varying the pressure and pulsating the skin surrounding the incision increases the amount of bodily fluid expressed to the incision.

Yet another problem associated with a finger massaging device is that the device is configured to receive a fingertip but not receive other body parts, such as for alternate site testing (AST). Therefore patients must repeatedly lance their fingertips in order to use the finger massaging device to urge or express fluid to the incision. Repeated lancing of fingertips can be painful due to the high concentration of nerve endings in the fingertips. Therefore, alternate sites on the body that have fewer nerve endings may provide a less painful area to sample blood or other body fluids. However, these alternate sites may produce less body fluid when lanced as compared to fingertips. Therefore, it is important to express an adequate sample of body fluid required for testing at an alternate site.

Thus, there remains a need for improvement in this field.

SUMMARY

One aspect of the present invention concerns a sampling device that includes a lancet, an expression member, a compression member, and a housing. The expression member includes a band that is movable between a relaxed position and a contracted position. At least a portion of the expression member is resilient.

A further aspect concerns a sampling device. The device includes an expression member that has at least one expression lobe. The sampling device also includes a compression member that has at least one compression lobe configured to contact and traverse the expression lobe on the expression member.

Another aspect concerns a sampling device. The device includes an expression member, a compression member, and a housing. The expression member is movable between a relaxed position and a contracted position over an incision in skin. The compression member engages the expression member to pulsate the expression member. The expression member is at least partially resilient.

Still yet another aspect concerns a method of expressing a body fluid. The method includes positioning a sampling device over an incision in skin and expressing body fluid from the incision with the sampling device by repeatedly squeezing and/or compressing the skin near the incision.

Further forms, objects, features, aspects, benefits, advantages, and embodiments of the present invention will become apparent from a detailed description and drawings provided herewith.

BRIEF DESCRIPTION OF THE DRAWINGS

FIG. 1 is an end view of a sampling device according to one embodiment of the present invention in a relaxed position.

FIG. 2 is a cross sectional view of the FIG. 1 device depicting only an expression member taken along line 2-2 in FIG. 1.

FIG. 8 is an end view of a sampling device according to a second embodiment of the present invention in the relaxed position.

FIG. 9 is a cross sectional view of the FIG. 8 device depicting only an expression member taken along line 9-9 in FIG. 8.

DESCRIPTION OF THE SELECTED EMBODIMENTS

Figure 3:
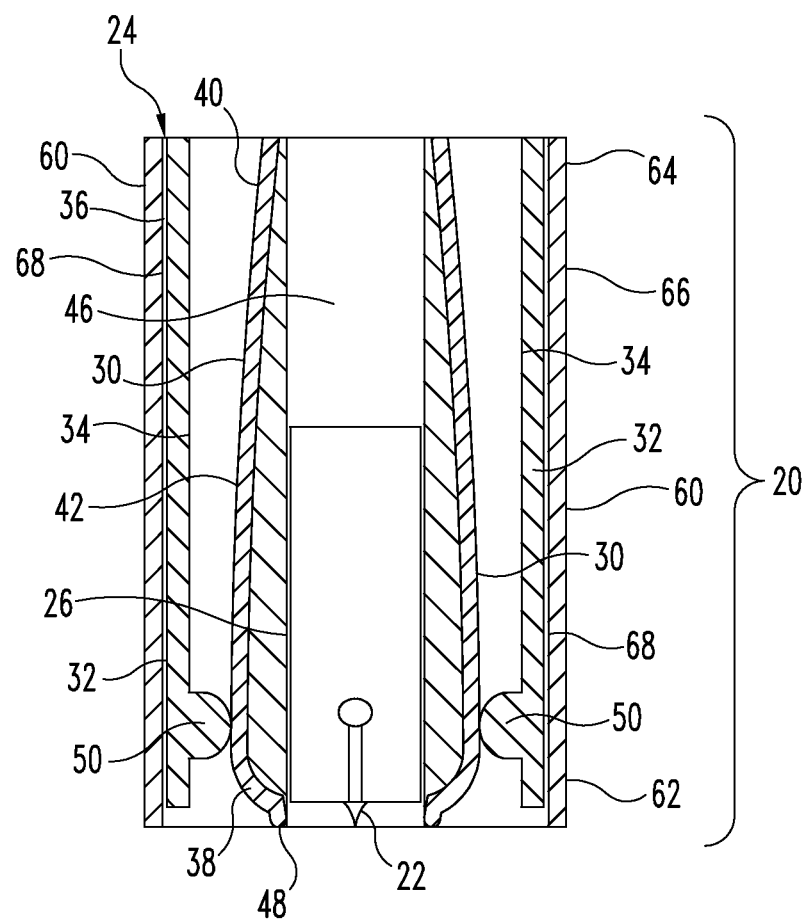
FIG. 3 is a cross sectional view of the FIG. 1 device taken along line 3-3 in FIG. 1.
Figure 5:
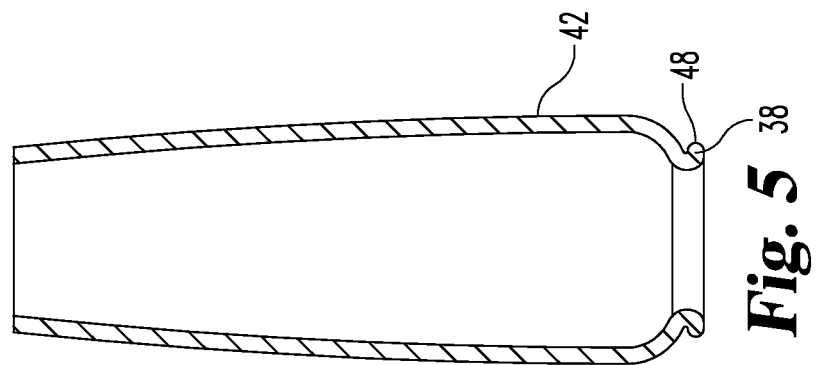
FIG. 5 is a cross sectional view of the FIG. 1 device depicting only an expression member taken along the line 5-5 in FIG. 4.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

One embodiment of the present invention generally concerns a sampling device that increases the amount of bodily fluid that flows into an incision. The sampling device operates to allow automatic milking or pumping of the bodily fluid by the force of an automatic mechanism engaging the sampling device. However, the sampling device also operates to allow manual milking of bodily fluid as the user engages the sampling device. The sampling device is operable to express body fluid from the incision with a compressive force and/or a rotational force applied to the sampling device. In one form, the sampling device pulsates to express body fluid from the incision. In another embodiment, body fluid is expressed from the incision by repeatedly applying a compressive force to the skin and/or applying a rotational force to the sampling device in a varying pattern.

A sampling device 20 according to one embodiment, among others, of the present invention will now be described with reference to FIGS. 1 and 3. As depicted in FIG. 3, the sampling device 20 includes a lancet or incision forming member 22 for forming an incision in skin, an expression device 24 for expressing bodily fluid from the incision, and a test device or strip 26 for drawing the bodily fluid via capillary action and testing the bodily fluid from the incision. As should be appreciated, the expression device 24 expresses bodily fluid from the incision and the test device 26 draws the expressed bodily fluid onto the test device 26. In one embodiment, the sampling device 20 is integrated with an integrated test strip of the type, for example, as disclosed in U.S. Publication No. 2002/0103499 Alto Perez et al., published on Aug. 1, 2002 (U.S. patent application Ser. No. 10/054,270, filed Jan. 22, 2002), which is hereby incorporated by reference in its entirety. Nevertheless, it should be appreciated that other types of sampling devices may be used. A flat lancet 22 is shown in FIG. 3 but other devices can be used to form an incision. In FIG. 1, the expression device 24 includes an expression member 30 for squeezing and/or compressing the skin near the incision and a compression member 32 for engaging the expression member 30. The compression member 32 includes an expression facing surface 34 for receiving the expression member 30 and a housing facing surface 36 opposite the expression facing surface 34.

As depicted in FIGS. 2 and 3, the expression member 30 includes a skin contacting portion 38 that is configured to contact the skin surrounding an incision, a distal portion 40 opposite the skin contacting portion 38, and a compression member facing surface 42 from which one or more expression nubs 44 extend. The shape of expression member 30 may vary, for example expression member 30 may be a tube, barrel, frustoconical, or any other shape that allows expression member 30 to express bodily fluid to an incision.

As can be seen from FIGS. 1 and 3, expression member 30 includes a passageway 46 that has a circular cross sectional shape for receiving the lancet 22 and through which lancet 22 extends during lancing. It should be appreciated that passageway 46 may be various geometric shapes as desired. In one form, the expression member 30 includes an annular band 48 near the skin contacting portion 38 for squeezing and/or compressing the skin near the incision. As should be appreciated, the band 48 may be other shapes such as, but not limited to, rectangular, oval, trapezoidal, or elliptical, to name a few. In one form, the annular band 48 is made of a resilient material, such as, but not limited to, silicone rubber or butyl rubber. However, it should be appreciated that the annular band 48 may be made of other forms of resilient material.

In FIGS. 2 and 3, the skin contacting portion 38 extends from the annular band 48 towards the distal portion 40 and the skin contacting portion 38 is configured to compress or relax as the annular band 48 is compressed or relaxed. Further, the skin contacting portion 38 has a generally circular shape to surround the annular band 48, but it should be appreciated that in other embodiments, the skin contacting portion 38 may be shaped differently. By way of non-limiting examples, the skin contacting portion 38 may be rectangular, oval, trapezoidal, elliptical, or any other shape that may surround the annular band 48. Further the skin contacting portion 38 can be textured to improve expression of fluid from the incision and/or grip of the skin surrounding the incision. For example, the skin contacting portion 38 may have castled, spiraled, or stepped surface, to name a few. In the illustrated embodiment, the skin contacting portion 38 is made of a resilient material, such as, but not limited to, silicone rubber or butyl rubber. However, it is contemplated that the skin contacting portion 38 may be made of other forms of resilient material.

As shown in FIG. 1, the expression nubs 44 extend radially outward from the compression facing surface 42 to contact one or more compression lobes 50 extending radially inward from the expression facing surface 34. As depicted in FIG. 1, a plurality of expression nubs 44 extend from the compression member facing surface 42. However, it should be appreciated that in other embodiments, one or more expression nubs 44 may extend from the compression member facing surface 42. By way of non-limiting examples, the expression nubs 44 may be semi-circular, semi-elliptical, rectangular, or any other shape that allows the expression nubs 44 to contact the compression lobes 50.

Figure 4:
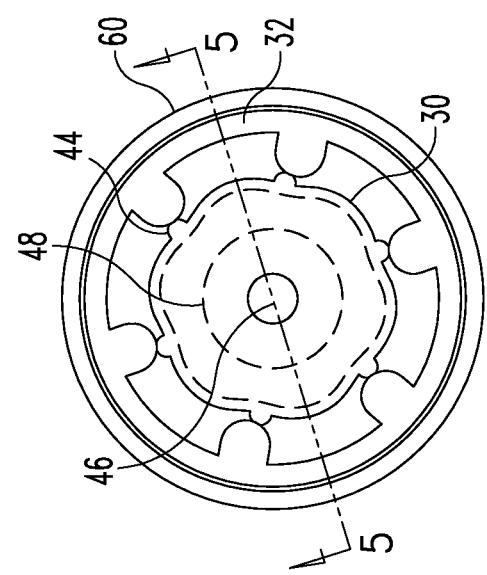
FIG. 4 is an end view of the FIG. 1 sampling device in a constricted position.

As can be seen from FIGS. 1 and 4, the semi-circular shaped compression lobes 50 are configured to contact and traverse the expression nubs 44. In FIG. 1, the compression member 32 has a plurality of compression lobes 50 extending from the expression facing surface 34. However it should be appreciated that in other embodiments, one or more compression lobes 50 may extend radially inward from the expression facing surface 34. As shown, an equal number of the compression lobes 50 are evenly spaced on the expression facing surface 34 with respect to the expression nubs 44 spaced on the compression member facing surface 42. In another form, the expression nubs 44 and the compression lobes 50 can be unevenly spaced such that the compression lobes 50 contact and traverse the expression nubs 44 wherein the annular band 48 is compressed in an asymmetrical pattern. As should be appreciated, the uneven spacing of the expression nubs 44 and compression lobes 50 varies the pulsating pattern of the annular band 48. In FIG. 1, the compression lobes 50 have a generally rounded shape but it should be appreciated that in other embodiments the compression lobes 50 may be a semi-oval shape, a rectangular shape, an elliptical shape, or any other shape that will contact and traverse the expression nubs 44. The shape of the expression nubs 44 and the compression lobes 50 allow them to slide over one another.

Figure 6:
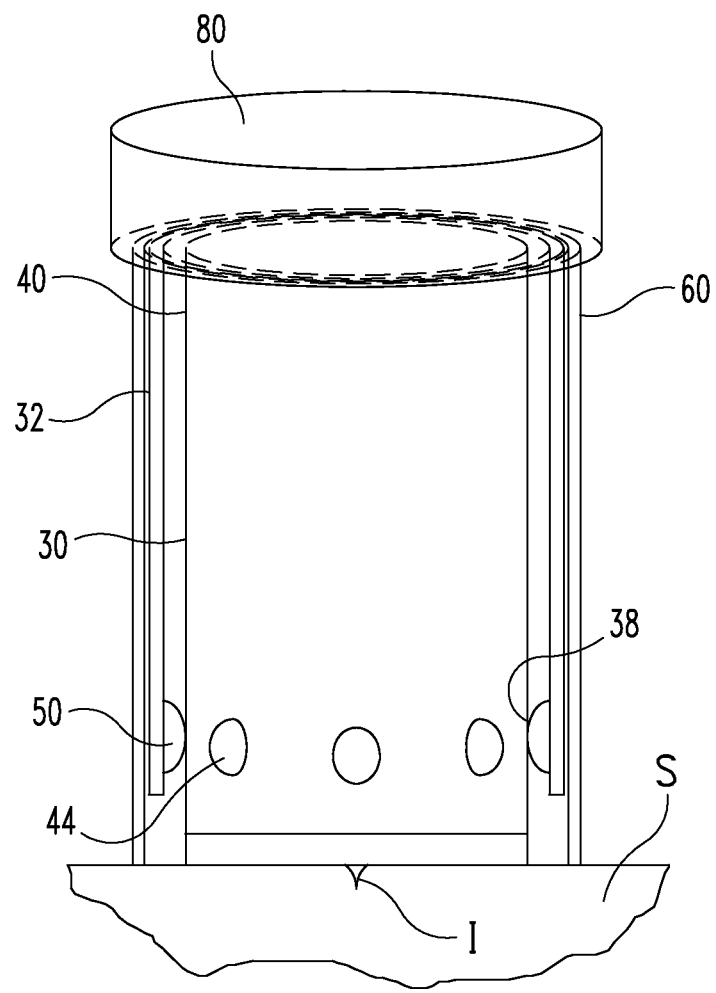
FIG. 6 is a side partial, cross sectional view of the FIG. 1 sampling device in the relaxed position in contact with the skin.

As depicted in FIG. 3, the sampling device 20 includes a housing 60 that holds the compression member 32 and allows the compression member 32 to engage the expression member 30. The housing 60 includes a skin contacting portion 62 for contacting the skin near the incision and a distal portion 64 opposite the skin contacting portion 62. The housing 60 also includes an exterior surface 66 for a user or a mechanical device to grasp and an interior surface 68 for nesting with the housing facing surface 36 of the compression member 32. In one embodiment, the housing 60 includes a passageway 70 that is configured to receive the compression member 32. In FIGS. 3 and 6, the housing 60 extends in a generally parallel relationship with respect to the expression member 30 and the compression member 32. In an alternate embodiment, the housing 60 has a concave shape that urges bodily fluid toward an incision as the skin contacting portion 62 contacts the skin near the incision.

As shown in FIGS. 1 and 3, the expression member 30, the compression member 32, and the housing 60 are three separate attachable elements. The expression member 30, the compression member 32, and the housing 60 each have a shape that allows the expression member 30 to nest within the compression member 32 and the compression member 32 to nest within the housing 60. In particular, the expression member 30, the compression member 32, and the housing 60 have a tubular shape that is beneficial as that shape is easy to manufacture and grasp by the user. It should be appreciated that the expression member 30, the compression member 32, and the housing 60 can be shaped differently in other embodiments.

The operation of the sampling device 20 according to one embodiment will now be described with reference to FIGS. 1, 4, 6, and 7. It should be appreciated that the expression device 24 illustrated in FIGS. 1 and 4, improves the speed and ease of use for a device that expresses bodily fluid for testing. With the expression member 30, compression member 32, and housing 60 combined into one device, the user will quickly be able to express bodily fluid from an incision by pulsating the skin surrounding the incision to milk or pump the fluid from the incision. Further, with the expression device 24, a user can express bodily fluid from a finger or an alternate site, such as, a forearm, leg, or earlobe to name a few body parts. The lancet 22 of the sampling device 20 forms an incision in skin, and the annular band 48 and the skin contacting portion 38 of the expression device 24 express fluid by applying pressure to the skin surrounding the incision, and/or squeezing or constricting the skin surrounding the incision. In the illustrated embodiment, the expression device 24 is configured to repeatedly apply or release pressure to the skin surrounding the incision and/or repeatedly squeeze or release the skin surrounding the incision. After a sufficient amount of bodily fluid is expressed by the expression device 24, the test device 26 is brought into contact with the bodily fluid so that the bodily fluid is drawn into the test device 26 via capillary action. Once the fluid is drawn into the test device 26, the test device 26 tests the collected bodily fluid. As should be appreciated, when a different type of sampling device is used, the bodily fluid can be collected and tested in a different manner.

FIGS. 1, 2, and 6 illustrate the relative positions of the expression member 30, compression member 32, and the housing 60 in a relaxed position such that the compression lobes 50 do not contact the expression nubs 44 as the sampling device 20 is placed on the user's skin S. A rotation mechanism or motor 80 is attached to the expression facing surface 34 and/or the housing facing surface 36 of the compression member 32 to rotate the compression member 32. In one form, the motor 80 holds the housing facing surface 36 as the motor 80 rotates the compression member 32. In a different form, the motor 80 attaches to the expression facing surface 34 to rotate the compression member 32. As should be appreciated in other embodiments, a user can manually rotate the compression member 32 without the assistance of a motor 80. For illustration, in FIGS. 6 and 7, a portion of the compression member 32 and a portion of the housing 60 are removed for clarity of the expression member 30. The annular band 48 and the skin contacting portion 62 are placed against the skin S. The annular band 48 is placed over the incision I.

Figure 7:
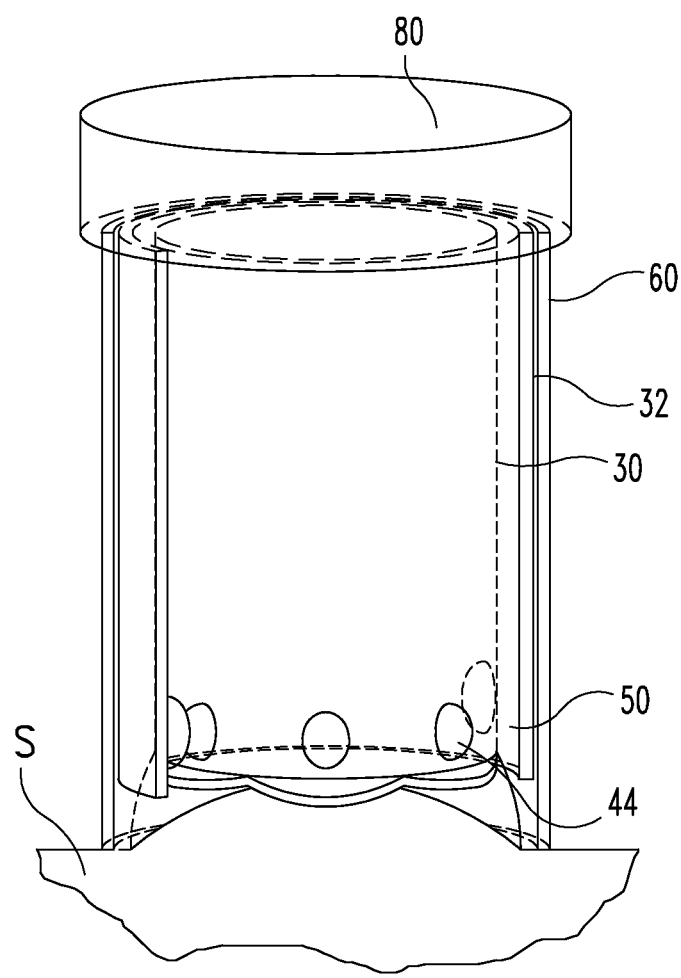
FIG. 7 is a side partial, cross-sectional view of the FIG. 1 sampling device in the constricted position in contact with the skin.

FIGS. 4 and 7 illustrate the relative positions of the expression member 30, the compression member 32, and the housing 60 in a contracted position after the motor 80 rotates the compression member 32 to engage the expression member 30. The compression lobes 50 contact and compress the expression nubs 44 causing the annular band 48 to expand and the passageway 46 to contract. The compression lobes 50 compress the expression nubs 44 causing the skin contacting portion 38 to contract.

FIGS. 1 and 6 also illustrate the relative positions of the expression member 30, the compression member 32, and the housing 60 after the motor 80 rotates the compression member 32 such that the compression lobes 50 traverse the expression nubs 44. In the illustrated embodiment, the annular band 48 contracts and the passageway 46 expands to its relaxed position. Also, as depicted in FIG. 2, the skin contacting portion 38 expands to its relaxed position. In one form, the rotational force applied to compression member 32 and the compressive force applied to the expression member 30 are repeatedly applied and released until an adequate supply of bodily fluid is expressed to the incision I. Further, the pulsation of the annular band 48 around the incision I continuously urges blood to flow to the incision I as the pressure is applied and released. The repeated milking or pumping of the skin S around the incision I allows the bodily fluid to flow into the incision I. In an alternate embodiment, the concave shape of the housing 60 aids in expressing body fluid to the incision I as the rotational force is applied to compression member 32. As should be appreciated, the repeated application of a rotational force to compression member 32 causes the skin contacting portion 38, the passageway 46, and the annular band 48 to expand and/or contract over the incision I.

Figure 10:
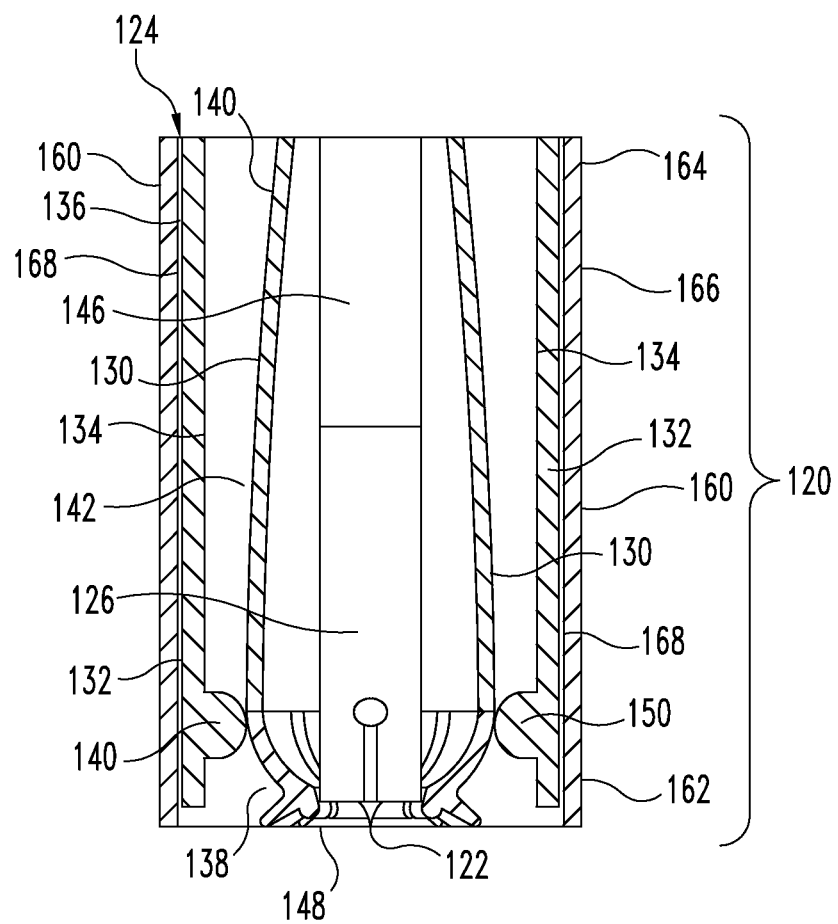
FIG. 10 is a cross sectional view of the FIG. 8 device taken along line 10-10 in FIG. 6.

Illustrated in FIGS. 8 and 10 is a sampling device 120 according to an alternate embodiment of the present invention. Sampling device 120 includes a lancet 122 for forming an incision, an expression device 124 for expressing bodily fluid from the incision, and a test device or strip 126 for drawing the bodily fluid via capillary action and testing the bodily fluid from the incision. As should be appreciated, the expression device 124 expresses bodily fluid from the incision and the test device 126 draws the expressed bodily fluid onto the test device 126. A flat lancet 122 is shown in FIG. 7 but other devices can be used to form an incision. Expression device 124 includes an expression member 130 for squeezing and/or compressing the skin near the incision. Sampling device 120 also includes a compression member 132 to engage the expression member 130. The compression member 132 includes an expression facing surface 134 for receiving the expression member 130 and a housing facing surface 136 opposite the expression facing surface 134.

Figure 12:
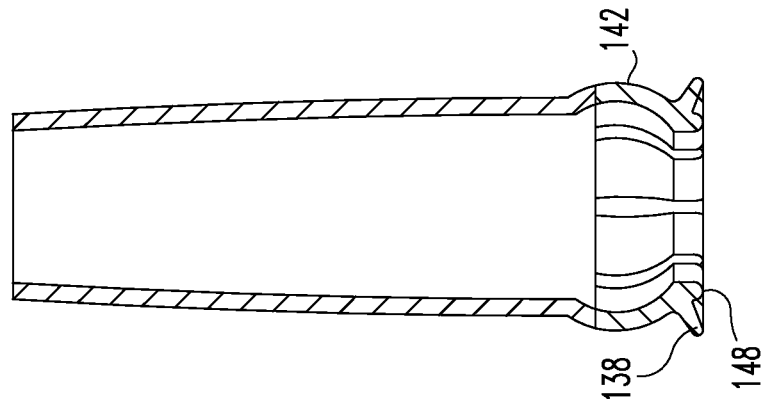
FIG. 12 is a cross sectional view of the FIG. 8 device depicting only an expression member taken along line 12-12 in FIG. 11.

In FIGS. 9 and 10, expression member 130 includes a skin contacting portion 138 that is configured to contact the skin surrounding the incision, a distal portion 140 opposite the skin contacting portion 138, and a compression member facing surface 142 for which one or more expression lobes or nubs 144 extend. Expression member 130 also includes a passageway 146 that has a circular cross sectional shape for receiving lancet 122. As should be appreciated, passageway 146 can be various geometric shapes as desired. In the illustrated embodiment, the expression member 130 includes one or more petals or fingers 148 near the skin contacting portion 138 for squeezing and/or compressing the skin near the incision. In one form, the fingers 148 are made of a resilient material, such as, but not limited to silicone rubber or butyl rubber. However, it is contemplated that the fingers 148 can be made of other forms of resilient material. In FIG. 9, the fingers 148 are configured in a contracted semi-circular shape. In FIG. 12, the fingers 148 are configured in a dilated semi-circular shape. The skin contacting portion 138 extends from the fingers 148 towards the distal portion 140 and the skin contacting portion 138 is configured to compress or relax as the fingers 148 are compressed or relaxed. In one form, the skin contacting portion 138 and the fingers 148 are configured to pulsate the skin surrounding the incision. In FIG. 9, the skin contacting portion 138 has a circular shape to surround the fingers 148, but it should be appreciated that in other embodiments the skin contacting portion 138 may be another shape. The skin contacting portion 138 is made of a resilient material, such as, but not limited to silicone rubber or butyl rubber. However, it is contemplated that the skin contacting portion 138 may be made of other forms of resilient material.

As shown in FIG. 8, the semi-circular shaped expression nubs 144 extend radially outward from the compression facing surface 142 to contact one or more compression lobes 150 extending radially inward from expression facing surface 134. As should be appreciated, the semi-circular shape of expression nubs 144 allows the compression lobes 150 to contact and traverse the expression nubs 144. By way of non-limiting examples, the expression nubs 144 may be semi-circular, semi-elliptical, rectangular, or any other shape that allows the expression nubs 144 and the compression lobes 150 to slide over one another.

The semi-circular shaped compression lobes 150 extend radially inward from the expression facing surface 134 and the compression lobes 150 are configured to contact and traverse the expression nubs 144. As depicted in FIG. 8, the compression member 132 has a plurality of compression lobes or bulges 150 extending from the expression facing surface 134. However, it should be appreciated that in other embodiments, one or more compression lobes 150 may extend radially inward from the expression facing surface 134. In one form, an equal number of the compression lobes 150 are evenly spaced on the expression facing surface 134 with respect to the expression nubs 144 spaced on the compression member facing surface 142. In another form, an unequal number of compression lobes 150 and expression nubs 144 are spaced such that the compression lobes 150 contact and traverse the expression nubs 144 wherein the fingers 148 are compressed in an asymmetrical pattern. As should be appreciated, the uneven spacing of the expression lobes 144 and the compression lobes 150 varies the pulsating pattern of the fingers 148. In the illustrated embodiment, the compression lobes 150 have a generally semi-circular shape but it should be appreciated that in other embodiments the compression lobes 150 may be a different shape. The shape of the expression lobes 144 and compression lobes 150 allow them to slide over one another.

Figure 13:
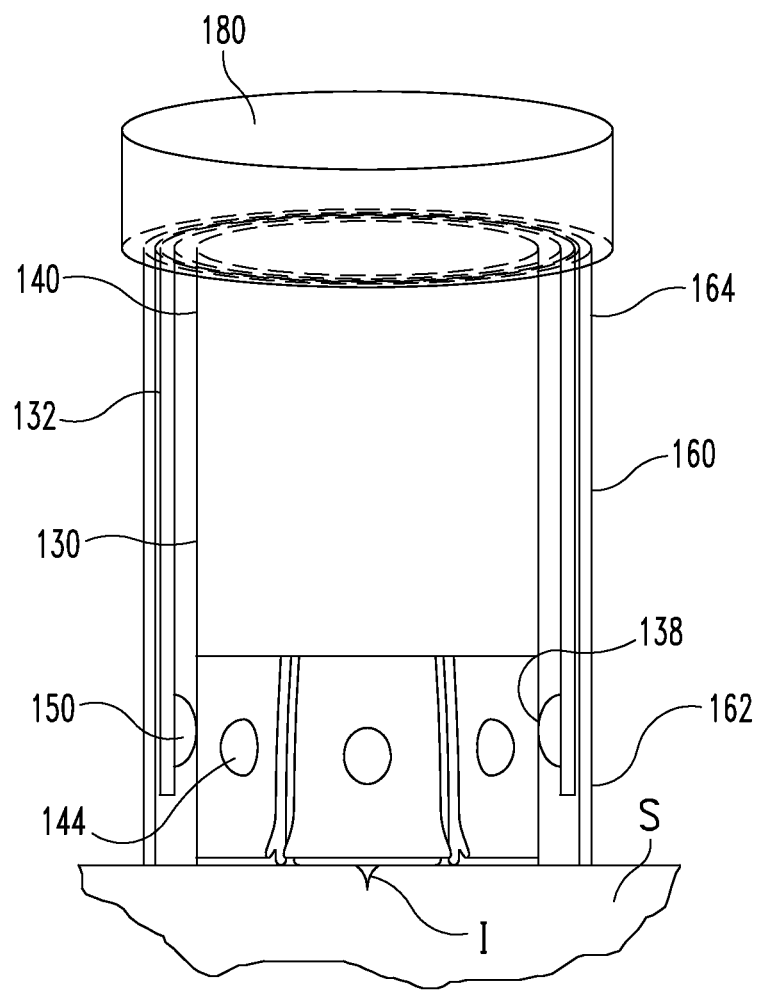
FIG. 13 is a side partial, cross-sectional view of the FIG. 8 sampling device in the relaxed position in contact with the skin.

As depicted in FIGS. 8 and 13, the sampling device 120 includes a housing 160 that holds the compression member 132 and allows the compression member 132 to engage the expression member 130. The housing 160 includes a skin contacting portion 162 for contacting the skin near the incision and a distal portion 164 opposite the skin contacting portion 162. The housing 160 includes an exterior surface 166 for a user or a mechanical device to grasp and an interior surface 168 for nesting with the housing facing surface 136 of the compression member 132. In one embodiment, the housing includes a passageway 170 that is configured to receive the compression member 132. As depicted in FIG. 13, the housing 160 extends in a generally parallel relationship with respect to the expression member 130 and compression member 132. In an alternate embodiment, the housing 160 has a concave shape that urges bodily fluid toward an incision as the skin contacting portion 162 contacts the skin near the incision.

The operation of sampling device 120 according to an alternate embodiment will now be described with reference to FIGS. 8, 11, 13, and 14. FIGS. 8 and 13 illustrate the relative positions of the expression member 130, compression member 132, and the housing 160 in a relaxed position such that the compression lobes 150 do not contact the expression nubs 144 as the sampling device 120 is placed on the user's skin S. A rotation mechanism or motor 180 is attached to the expression facing surface 134 to rotate the compression member 132. In another form, a rotation mechanism 180 attaches to the housing facing surface 136 of the compression member 132 to rotate the compression member 132. In another form, a user can manually rotate the compression member 132 to engage the expression member 130. For illustration, in FIGS. 13 and 14, a portion of the compression member 132 and a portion of the housing 160 are removed for clarity of the expression member 130. The skin contacting portion 138 and the skin contacting portion 162 are placed against the skin S. The fingers 148 are placed over the incision I.

Figure 11:
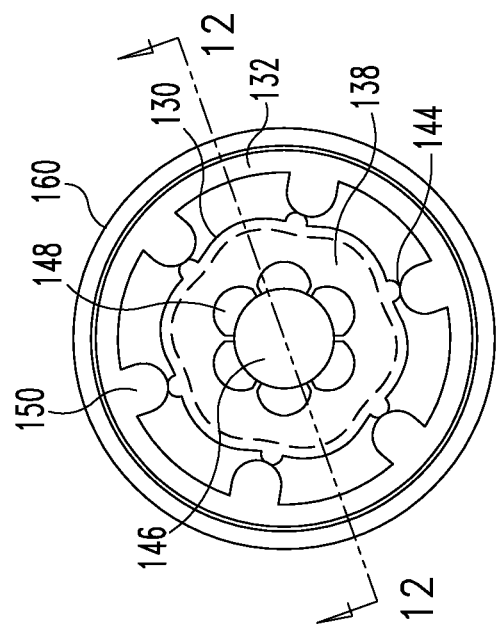
FIG. 11 is an end view of the sampling device according to a second embodiment of the present invention in the constricted position.
Figure 14:
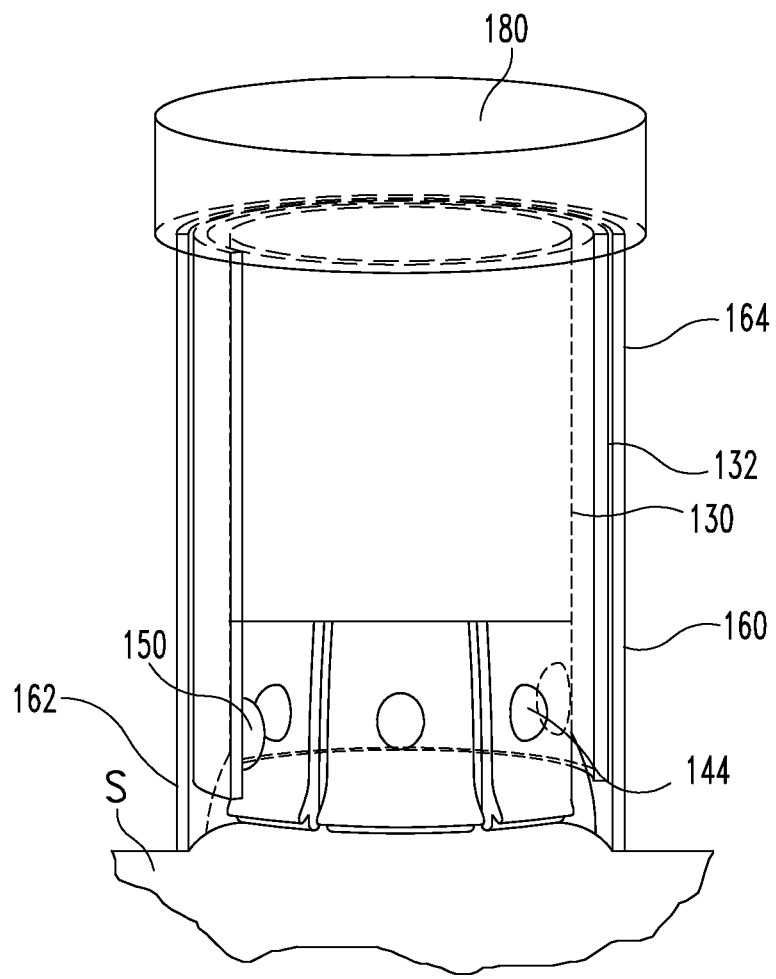
FIG. 14 is a side partial, cross-sectional view of the FIG. 8 sampling device in the constricted position in contact with the skin.

FIGS. 11 and 14 illustrate the relative positions of the expression member 130, the compression member 132, and the housing 160 after the motor 180 rotates the compression member 132 such that the compression lobes 150 contact the expression nubs 144. The compression lobes 150 contact the expression nubs 144 causing the fingers 148 to expand and the passageway 146 to expand. FIGS. 8 and 13 also illustrate the relative positions of the expression member 130, the compression member 132, and the housing 160 after the compression member 132 has been rotated such that the compression lobes 150 traverse the expression nubs 144 and the compression lobes 150 are no longer contacting the expression nubs 144. In FIG. 8, the fingers 148 and the passageway 146 contract to a relaxed position. Also, as depicted in FIG. 8, the skin contacting portion 138 expands to a relaxed position. In one form, the rotational force applied to compression member 132 and/or the compressive force applied to compression member 132 are repeatedly applied and released until an adequate supply of bodily fluid is expressed to the incision I. In another form the fingers 148 pulsate as the compression lobes 150 and expression nubs 144 slide over each other. It is contemplated that fingers 148 can pulsate in an asymmetrical pattern. By way of non-limiting example, an uneven number of compression lobes 150 and expression nubs 144 sliding over each other or an uneven spacing of the compression lobes 150 or expression nubs 144 can produce an asymmetrical pattern of pulsation. In an alternate embodiment, the concave shape of the housing 160 aids in expressing body fluid to the incision I as the rotational force is applied to the compression member 132. As should be appreciated, the repeated application of a rotational force to compression member 132 causes the skin contacting portion 138, the passageway 146, and the fingers 148, to expand and/or contract over the incision I.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. All publications, patents, and patent applications cited in this specification are herein incorporated by reference as if each individual publication, patent, or patent application were specifically and individually indicated to be incorporated by reference and set forth in its entirety herein.

What is claimed is:

1. A method of expressing a body fluid, comprising:
positioning a sampling device having an expression member and a compression member over an incision in skin, the expression member having a resilient band for contacting the skin surrounding the incision, the expression member including a plurality of expression lobes and the compression member including a plurality of compression lobes; and
repeatedly rotating the compression member about the expression member between a first position and a second position, wherein the first position includes the plurality of compression lobes contacting the plurality of expression lobes to deform the resilient band of the expression member, the deformed resilient band squeezing and compressing the skin that surrounds the incision to express bodily fluid from the incision, and wherein the second position includes the plurality of compression lobes contacting the expression member and releasing pressure on the skin that surrounds the incision, the resilient band returning to an undeformed shape.

2. The method of claim 1, further comprising:
compressing the skin that surrounds the incision with a housing to urge the bodily fluid to the incision, the housing contacting the skin surrounding the incision.

3. The method of claim 1, further comprising:
collecting the bodily fluid with a test strip of the sampling device.

4. The method of claim 1, further comprising:
releasing pressure on the skin that surrounds the incision as the plurality of compression lobes traverse the plurality of expression lobes.

5. The method of claim 4, further comprising:
varying the deformation of the expression member to squeeze and compress the skin that surrounds the incision in an asymmetrical pattern.

6. A method of expressing a body fluid, comprising:
positioning a sampling device having an expression member and a compression member over an incision in skin, the expression member having a deformable end portion for contacting the skin surrounding the incision, the expression member includes a plurality of expression lobes and the compression member includes a plurality of compression lobes; and
repeatedly contacting and traversing the plurality of expression lobes with the plurality of compression lobes as the compression member is rotated about the expression member from a first position to a second position, wherein the first position includes deforming the deformable end portion, the deformed end portion pulsating the skin surrounding the incision to pump bodily fluid from the incision, and wherein the second position includes the deformed end portion returning to an undeformed shape, the undeformed end portion releasing pressure on the skin surrounding the incision.

7. The method of claim 6, wherein the deformable end portion includes a plurality of resilient fingers configured in a semi-circular shape; and
wherein pulsating the skin surrounding the incision includes dilating the plurality of resilient fingers as the plurality of compression lobes contact the plurality of expression lobes and contracting the plurality of resilient fingers as the plurality of compression lobes traverse the plurality of expression lobes.

8. The method of claim 6, further comprising:
compressing the skin that surrounds the incision with a housing to urge the bodily fluid to the incision, the housing contacting the skin surrounding the incision.

9. A sampling device, comprising:
an incision forming member configured to form an incision in skin;
an expression member defining an expression passageway through which the incision forming member extends, the expression member having a deformable end portion having a plurality of resilient fingers configured to move from a relaxed position wherein the plurality of resilient fingers contact the skin that surrounds the incision to a contracted position wherein the plurality of resilient fingers contact and squeeze the skin that surrounds the incision, the expression member having a plurality of expression lobes;
a compression member defining a compression passageway to receive the expression member, the compression member configured to rotate about the expression member, the compression member having a plurality of compression lobes configured to contact the plurality of expression lobes wherein the plurality of resilient fingers compresses from the relaxed position to the contracted position to squeeze the skin that surrounds the incision; and
a housing defining a housing passageway to receive the compression member, the housing having a skin contacting portion to contact the skin that surrounds the incision to urge bodily fluid toward the incision.

10. The sampling device of claim 9, wherein the housing has a concave shape.

11. The sampling device of claim 9, wherein:
the expression member is nested in the compression member; and
the compression member is nested in the housing.

12. The sampling device of claim 11, wherein:
the expression member is a tubular shape;
the compression member is a tubular shape; and
the housing is a tubular shape.

13. The sampling device of claim 9, further comprising a testing element configured to test bodily fluid expressed from the incision.

* * * * *